United States Patent [19]

Ruschke

[11] 4,452,473
[45] Jun. 5, 1984

[54] LUER CONNECTION SYSTEM

[75] Inventor: Ricky R. Ruschke, McHenry, Ill.

[73] Assignee: Baxter Travenol Laboratories, Inc., Deerfield, Ill.

[21] Appl. No.: 401,571

[22] Filed: Jul. 26, 1982

[51] Int. Cl.³ .................. F16L 35/00; F16L 25/00
[52] U.S. Cl. ........................ 285/81; 285/332;
   285/386; 285/92; 604/905; 604/283; 604/241
[58] Field of Search .............. 285/332, 81, 82, 84,
   285/85, 86, 92, 386, 32; 604/905, 283, 241, 242,
   243, 272

[56] References Cited

U.S. PATENT DOCUMENTS

| | | | |
|---|---|---|---|
| 2,347,469 | 4/1944 | Dies | 285/332 |
| 2,443,394 | 6/1948 | Le Clair | 285/82 X |
| 2,454,557 | 11/1948 | Jacobson | 285/332 X |
| 2,775,801 | 7/1956 | Morando . | |
| 2,988,385 | 6/1961 | Foelster et al. | 285/179 |
| 3,514,131 | 5/1970 | McKinney | 285/332 |
| 3,542,024 | 11/1970 | Burke | 604/241 |
| 3,876,234 | 4/1975 | Harms | 285/332 X |
| 3,984,133 | 10/1976 | Bird | 285/322 |
| 4,046,479 | 9/1977 | Paley | 285/332 X |
| 4,076,285 | 2/1978 | Martinez | 285/332 |
| 4,133,312 | 1/1979 | Burd | 285/332 X |
| 4,266,815 | 5/1981 | Cross | 285/332 X |
| 4,296,949 | 10/1981 | Muetterties et al. | 285/386 X |
| 4,369,781 | 1/1983 | Gilson et al. | 285/332 X |

FOREIGN PATENT DOCUMENTS

| | | | |
|---|---|---|---|
| 1204896 | 11/1965 | Fed. Rep. of Germany | 285/332 |
| 2127866 | 10/1972 | France . | |
| 1397493 | 6/1975 | United Kingdom . | |
| 617654 | 7/1978 | U.S.S.R. | 285/332 |

Primary Examiner—Richard J. Scanlan, Jr.
Attorney, Agent, or Firm—John P. Kirby, Jr.; Bradford R. L. Price; George H. Gerstman

[57] ABSTRACT

A luer connection system is provided in which a male luer connector (20) has a main body portion (22) and a front luer portion (24) with a locking ring (42) that is axially slidable along the main body portion (22). The locking ring (42) is adapted to threadedly engage a mating female luer device (52). A collar (26) is carried by the male luer connector (20) between the main body portion (22) and the front luer portion (24). The luer connector has a flexible member (38) which flexes to a stressed position when the locking ring (42) is in threaded engagement with the mating female luer device (52). In this manner, there is some stress provided in the threaded engagement to prevent the locking ring (42) from inadvertently disengaging.

19 Claims, 17 Drawing Figures

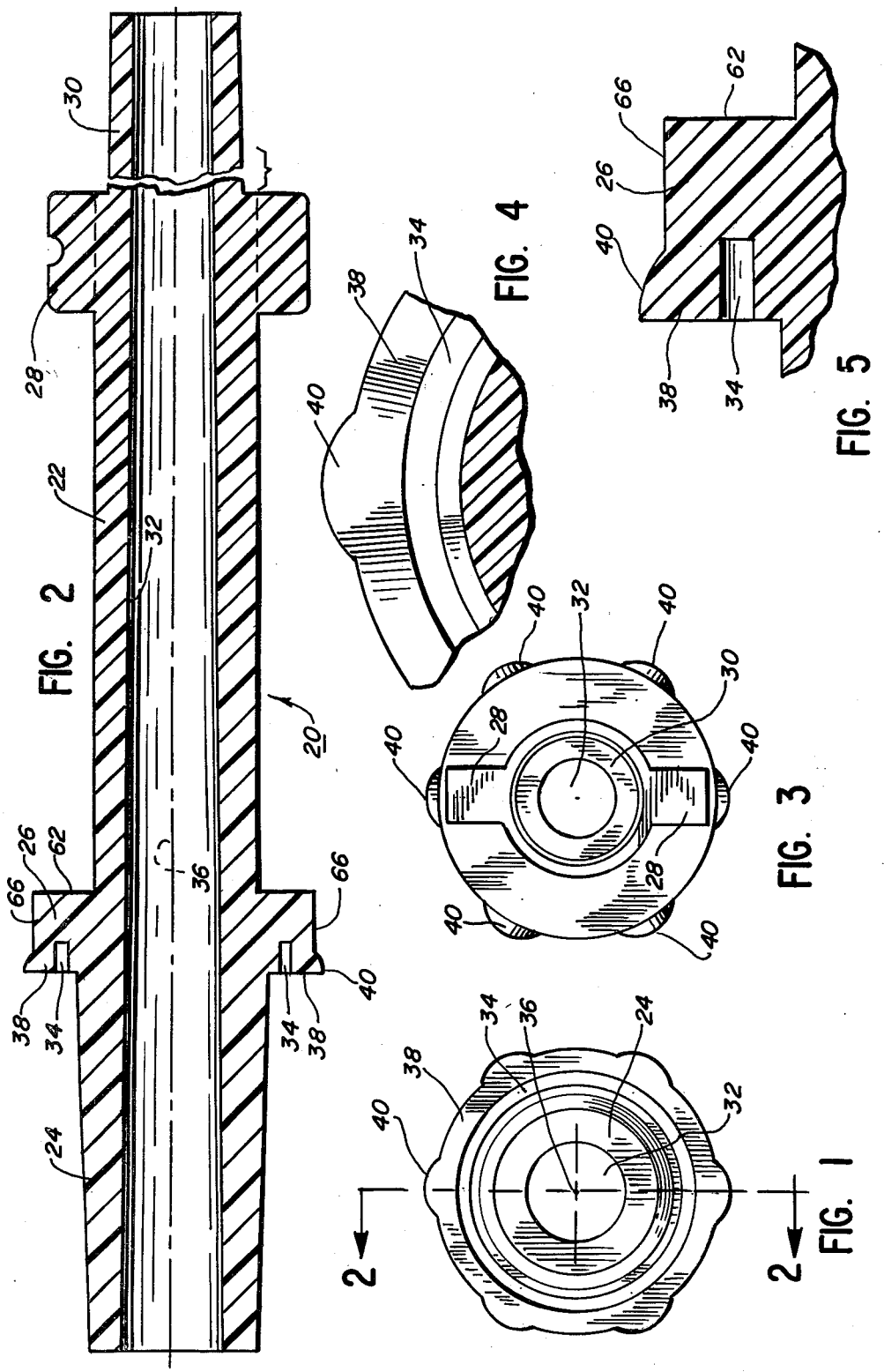

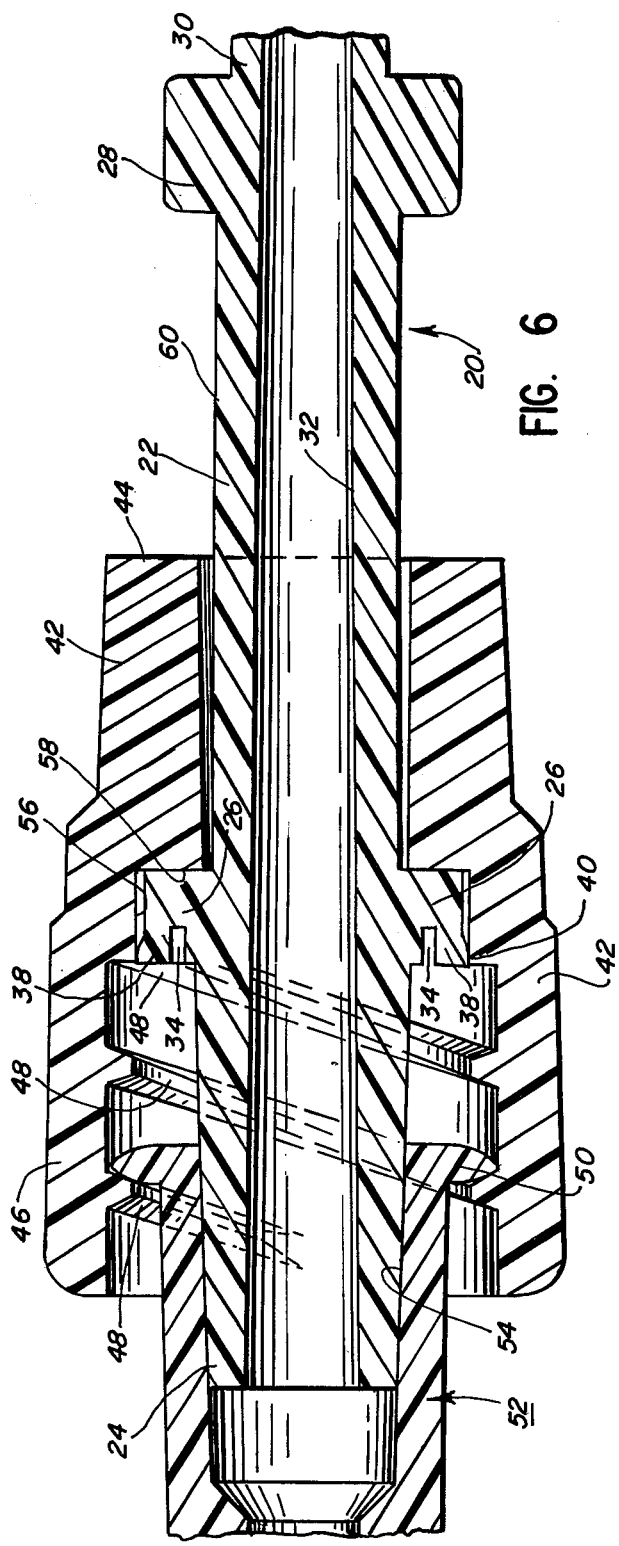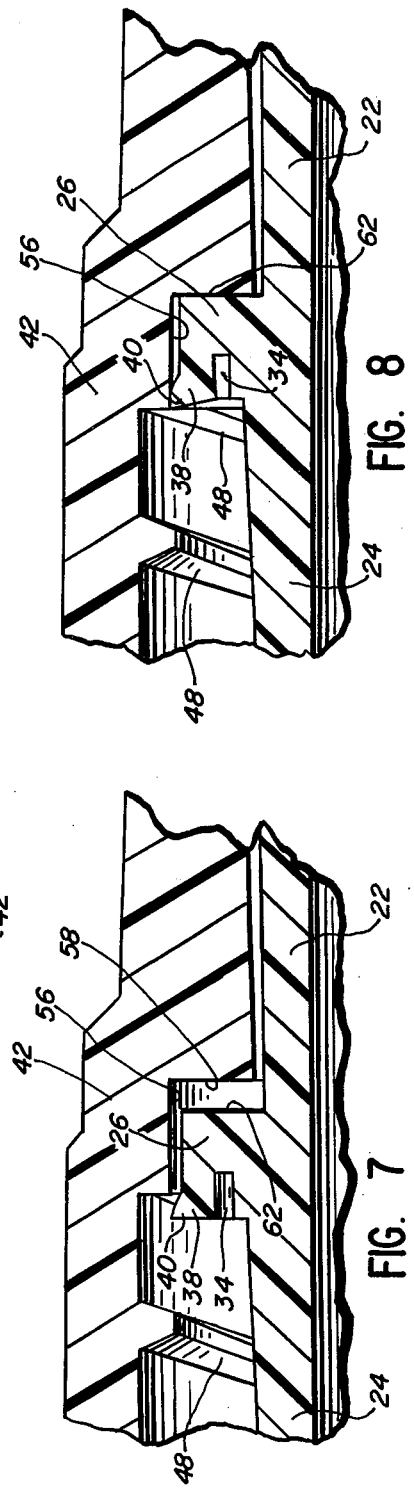

LUER CONNECTION SYSTEM

TECHNICAL FIELD

The present invention concerns a novel luer connection system for medical use where a secure, fluid-tight connection is desired.

BACKGROUND ART

Luer connection systems are widely used in medical environments, for example during administration of medicaments. During medical usage, it is, of course, important that a secure, fluid-tight connection be achieved. One type of luer connection comprises a plastic male luer connector, a plastic female luer connector, and an axially slidable locking ring carried by the male luer connector for threadedly engaging the female luer connector. On occasion the nurse administering the medicament has believed that the luer connection is insecure, because the locking ring tends to be easily disengageable. Occasionally the locking ring will disengage from the female luer connector, and there appears to be a lack of security.

I have discovered that a more effective luer connection system may be provided in which the locking ring carried by the male luer connector, once threadedly engaged with the female luer connector, is prevented from inadvertent disengagement. In this manner, once the nurse rotates the locking ring to threadedly engage the female luer connector, the locking ring will be maintained in place without inadvertent disengagement, until the nurse purposely uncouples the locking ring by expressly turning it in the disengagement direction.

Therefore, it is an object of the present invention to provide a luer connection system in which an axially slidable locking ring is prevented from inadvertent disengagement once it is properly engaged.

Another object of the present invention is to provide a secure luer connection system in which resilient portions of the locking ring security system will not be damaged during use.

A further object of the present invention is to provide a luer connection system which is simple in operation and efficient to manufacture.

Other objects and advantages of the present invention will become apparent as the description proceeds.

DISCLOSURE OF THE INVENTION

In accordance with the present invention, a luer connection system is provided in which a male luer connector having a main body portion and a front luer portion is adapted for coupling to a mating female luer device. The male luer connector has a locking ring that is axially slidable along the main body portion and has interior threads which are adapted to threadedly engage the mating female luer device. A collar is carried by the luer connector between the main body portion and the front luer portion. The luer connector carries a flexible member which flexes to a stressed position when the locking ring is in threaded engagement with the mating luer device, to provide some stress in the threaded engagement. Such stress effectively prevents the locking ring from being inadvertently disengaged.

The flexible member is carried by either the collar or locking ring, to provide the resilient interrelationship between the collar and locking ring when the locking ring is in threaded engagement with the mating luer device. In accordance with certain embodiments of the invention, the flexible member comprises an integral portion of the collar defined by a slot. This collar portion flexes to a stressed position by its engagement with an interior wall of the locking ring with the locking ring is in threaded engagement with the mating luer device. In another embodiment of the invention, the flexible member comprises an interior portion of the locking ring defined by a slot. This interior locking ring portion flexes to a stressed position by its engagement with the collar when the locking ring is in threaded engagement with the mating luer device.

In the primary embodiment, the collar defines an annular slot that is radially spaced from the center of the collar. The flexible member comprises an annular portion of the collar that is radially outward of the slot and is flexible when it is urged by an interior wall of the locking ring to tend to close the slot, thereby creating a spring that is hinged near the inside end of the slot. The annular portion of the collar carries a plurality of spaced protuberances for engagement with an interior wall of the locking ring. The annular slot has a radial width that is sufficient to prevent the slot from being closed when the interior wall of the locking ring engages the annular portion of the collar. In this manner, the spaced protuberances will not be damaged by the action between the interior wall of the locking ring and the collar.

A more detailed explanation of the invention is provided in the following description and claims, and is illustrated in the accompanying drawings.

BRIEF DESCRIPTION OF THE DRAWINGS

FIG. 1 is a front view of a male luer connector constructed in accordance with the principles of the present invention.

FIG. 2 is a cross-sectional elevational view thereof.

FIG. 3 is a rear end view of the male luer connector of FIG. 1.

FIG. 4 is an enlarged, broken front view of the male luer connector of FIG. 1.

FIG. 5 is an enlarged, broken cross-sectional elevation of a portion of the collar carried by the male luer connector of FIG. 1.

FIG. 6 is a cross-sectional elevational view of a luer connection system constructed in accordance with the principles of the present invention.

FIG. 7 is an enlarged cross-sectional view of the locking ring-collar relationship when the locking ring is not in its forward position.

FIG. 8 is a similar cross-sectional view when the locking ring is in its forward position.

DETAILED DESCRIPTION OF THE ILLUSTRATIVE EMBODIMENT

Figure 9:
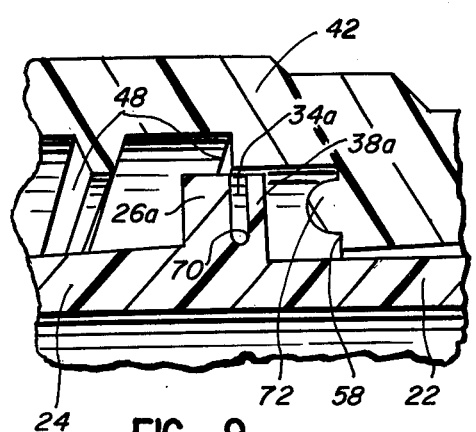
FIG. 9 is a cross-sectional view of the locking ring-collar arrangement of a second form of the invention.

Referring to FIGS. 1-3, a male luer connector 20 is shown therein. The male luer connector shown in FIGS. 1-3 is preferably formed of a rigid grade of polyvinyl chloride in an integral, one-piece construction. Male luer connector 20 comprises a main body portion 22, a front luer portion 24 that is tapered forwardly and inwardly, a collar 26 separating main body portion 22 from front luer portion 24, a ratchet member 28 at the rear end of main body portion 22, and a rear portion 30. In ordinary use, flexible tubing is connected to rear portion 30. The luer connector defines an axial bore 32 which extends through the entire luer connector as illustrated.

Collar 26 defines an annular slot 34 that is radially spaced from centerline 36 which is the centerline of bore 32 and also the centerline of collar 26. A flexible member 38 is formed by slot 34, which flexible member 38 comprises an annular portion of collar 26 that is radially outward of slot 34. Flexible member 38 carries six equally spaced protuberances 40 which are adapted for engagement with the upper interior wall of a locking ring to be described.

Now referring to FIGS. 6-8, locking ring 42, preferably formed of an ABS plastic, is illustrated therein. The locking ring 42 is axially slidable with respect to main body portion 22 and is slotted at its rear end portion 44 to receive ratchet member 28 thereby preventing relative rotation between the locking ring 42 and main body portion 22 when ratchet member 28 is received within the slot.

The front portion 46 of locking ring 42 carries interior threads 48 which are adapted to be threadedly received by an outwardly extending annular flange 50 carried by a female luer connector 52. Flange 50 may take the form of either spiral threads or the form of a single annular member as illustrated.

Female luer connector 52 comprises an open interior wall 54 that is tapered outwardly and forwardly (to the right with respect to FIG. 6) to snugly receive front luer portion 24 of male luer connector 20. The female luer connector 52 may comprise a catheter hub, an administration set connector or any other medical device for coupling to male luer connector 20.

In locking ring 42, rearward of threads 48, there is defined an upper interior wall 56 and a rear interior wall 58. Upper interior wall 56 is preferably generally parallel to the external surface 60 of main body portion 22 and rear interior wall 58 is generally perpendicular thereto.

Referring now to FIGS. 7 and 8, in FIG. 7 the locking ring 42 is shown in a rearward position wherein it has not threadedly engaged the female luer connector 52. In this position, it is seen that neither upper interior wall 56 nor rear interior wall 58 has engaged collar 26. However, referring to FIG. 8, it is seen that when the locking ring is moved forwardly so as to threadedly engage female luer connector 52, upper interior wall 56 engages protuberances 40 to cause flexible member 38 to flex, tending to close slot 34. The flexible member 38 is effectively hinged at the rear end of slot 34. Further, end wall 58 engages the rear 62 of collar 26, thereby preventing further forward movement of locking ring 42.

The dimensions of the collar and locking ring are such that when the locking ring engages the collar, the slot 34, will not be completely closed. If flexible member 38 were flexed by the locking ring so far that slot 34 would be closed, the wiping of upper interior surface 56 over protuberances 40 might tend to damage the protuberances 40. In order to prevent protuberances 40 from being damaged, the vertical width of slot 34 is greater than the amount of deflection of flexible member 38. For example, the radial width of slot 34 may be 0.012 inch and the maximum height of protuberance 40 may be 0.010 inch, with a 0.003 inch clearance between upper interior surface 56 of locking ring 42 and the peripheral surface 66 of collar 26. In this manner, the wiping action of upper interior surface 56 upon protuberances 40 will provide the flexure of flexible member 38 but will not be so great as to close the slots 34 and thereby cause damage to the protuberances 40.

In its forward position as illustrated in FIG. 8, when the locking ring is threadedly engaging the female luer connector 52, front luer portion 24 of male luer connector 20 will be snugly received by wall 54 of the female luer connector 52. Flexible member 38 will be stressed to provide some stress in the threaded engagement between the male luer connector and the female luer connector. By referring to the drawings, it is seen that the term "in the threaded engagement" is not limited to inside the threads 48 but includes adjacent interior walls. This stress that is created will prevent the locking ring 42 from inadvertently disengaging and will provide a relatively secure locking engagement.

In the embodiments of FIGS. 9-17, the same reference numerals as in the FIGS. 1-8 embodiments wil be used for the similar structural members.

Figure 10:
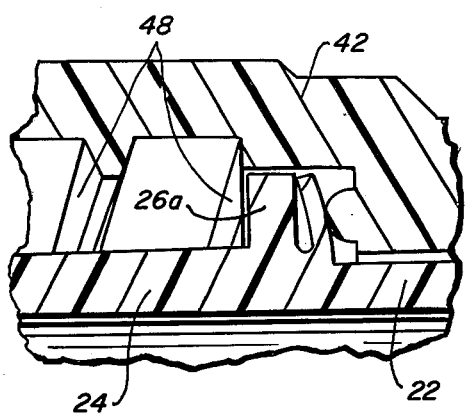
FIG. 10 is a similar cross-sectional view with the locking ring in its forward position.

Referring to the embodiment of FIGS. 9 and 10, the collar 26a defines an upwardly extending annular slot 34a which forms an upwardly extending flexible member 38a that is hinged generally at the bottom 70 of slot 34a. Rear interior wall 58 of locking ring 42 carries an annular protuberance 72 which does not engage flexible member 38a when the locking ring 42 is in a rearward position. However, when locking ring 42 is moved forwardly to threadedly engage the female luer connector, annular protuberance 72 will engage flexible member 38a to flex the flexible member 38a, thereby providing a stressed condition as illustrated in FIG. 10. This stressed condition will provide some stress on the threaded engagement between the male luer connector and the female luer connector to prevent inadvertent disengagement of the locking ring 42 from the female luer connector.

Figure 11:
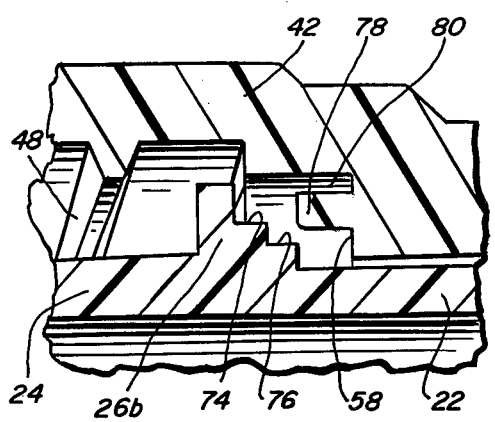
FIG. 11 is a cross-sectional view of the locking ring-collar relationship of a third form of the invention, with the locking ring in other than its forward position.
Figure 12:
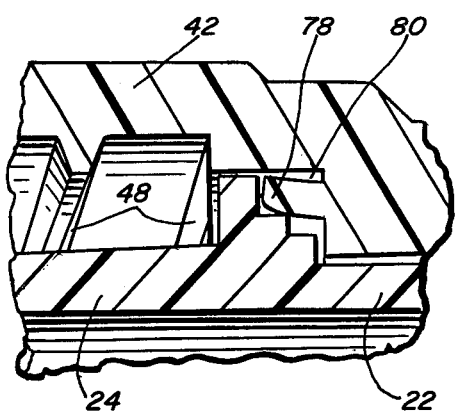
FIG. 12 is a similar cross-sectional view with the locking ring in its forward position.
Figure 13:
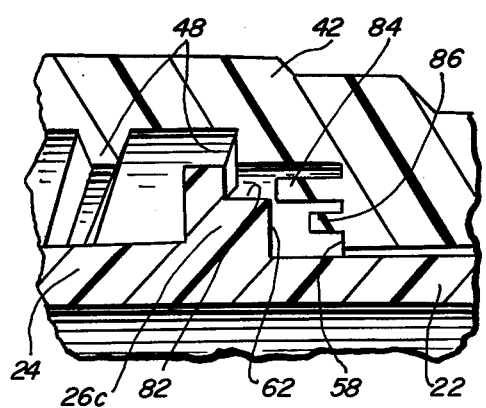
FIG. 13 is a cross-sectional view of a locking ring-collar arrangement in a fourth form of the invention.

In the embodiment of FIGS. 11 and 12, collar 26b includes an upper step 74 and a lower step 76. Rear interior wall 58 of locking ring 42 carries an annular protuberance 78, which is generally rectilinear in cross-sectional configuration. As illustrated in FIG. 11, when locking ring 42 is in its rearward position, there is no interengagement between protuberance 78 and collar 26b. However, as illustrated in FIG. 12, when the locking ring 42 is in its forward position threadedly engaging the female luer connector, protuberance 78 forms a flexible member which engages step 74 to flex upwardly, tending to close slot 80 which defines the protuberance or flexible member 78. This causes a stress condition thereby providing some stress on the threaded engagement between the male luer connector and the female luer connector, thereby preventing the locking ring 42 from inadvertently disengaging.

Other structural embodiments which operate in a similar manner to the operation as described above, are illustrated in FIGS. 13-17. For example, in FIG. 13 collar 28c includes a step 82 and the rear interior wall 58 of locking ring 42 carries a flexible member 84 and a stop member 86. When locking ring 42 is moved to its forward position, annular flexible member 84 will engage step 82 to cause flexing of the flexible member 84, thereby creating the appropriate stress relationship. Stop member 86 will abut back wall 62 of collar 28c to prevent excessive forward movement of locking ring 42.

Figure 14:
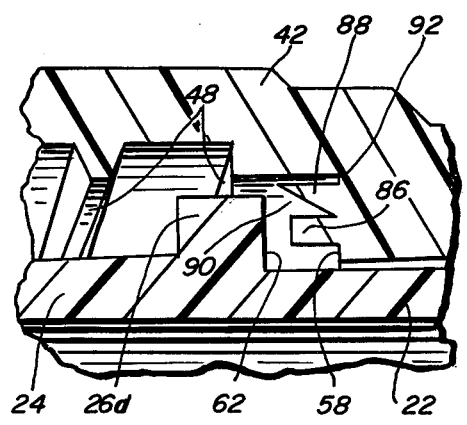
FIG. 14 is a cross-sectional view of the locking ring-collar arrangement in a fifth form of the invention.

In the FIG. 14 embodiment, rear interior wall 58 of locking ring 42 carries a flexible member 88 that has an underside taper 90 which rides upon collar 26d, tending to close slot 92. A stop member 86 is provided for engagement with rear wall 62 of collar 26d to prevent excessive forward movement of locking ring 42.

Figure 15:
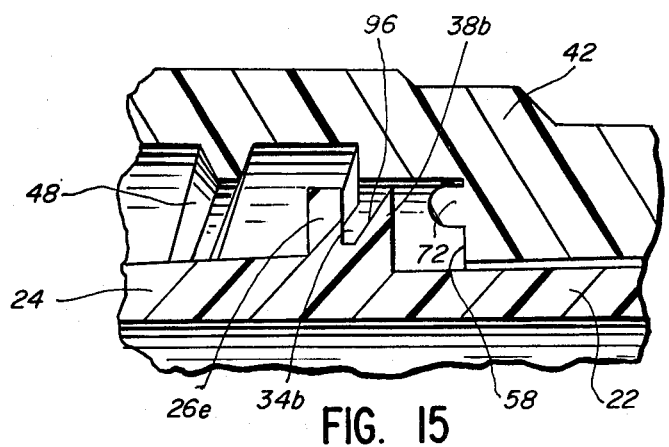
FIG. 15 is a cross-sectional view of the locking ring-collar arrangement in a sixth form of the invention.

In the FIG. 15 embodiment, collar 26e defines an upwardly extending slot 34b which forms a flexible member 38b having a tapered surface 96. Annular protuberance 72, carried by rear interior wall 58 of locking ring 42, engages flexible member 38b when the locking ring 42 is in its forward position, thereby flexing the flexible member 38b to tend to close slot 34b. This flexing creates the appropriate stress as discussed above.

Figure 16:
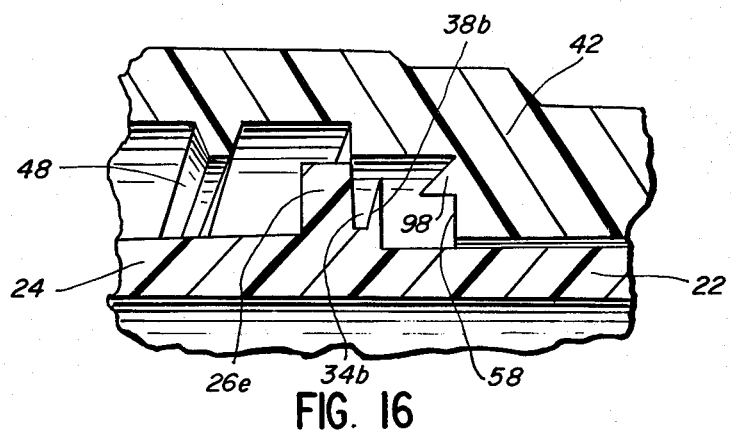
FIG. 16 is a cross-sectional view of the locking ring-collar arrangement in a seventh form of the invention.

In the FIG. 16 embodiment, rear interior wall 58 of locking ring 42 carries a protuberance 98 which has a generally triangular cross-sectional configuration. When the locking ring 42 is in its forward position, protuberance 98 will engage flexible member 38b to create the appropriate stress.

Figure 17:
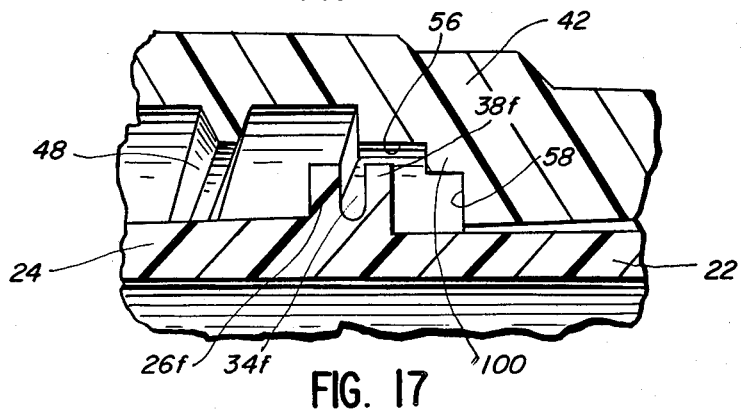
FIG. 17 is a cross-sectional view of the locking ring-collar arrangement in an eighth form of the invention.

In the embodiment of FIG. 17, collar 26f defines an upwardly extending slot 34f to form a flexible member 38f which extends upwardly as illustrated. A step 100 is provided between upper interior wall 56 of locking ring 42 and rear interior wall 58 of locking ring 42. When the locking ring is in its forward position, step 100 engages flexible member 38f to flex the flexible member 38f, thereby tending to close slot 34f and creating the appropriate stress relationship.

It is seen that a novel luer connection system has been provided in which a locking ring is axially slidable along the main body portion of the male luer connector for threaded engagement with the female luer connector, and a flexible member is carried by the male luer connector to create a stress tending to prevent inadvertent disengagement of the locking ring from the female luer connector. Although illustrative embodiments of the invention have been shown and described, it is understood that various modifications and substitutions may be made by those skilled in the art without departing from the novel spirit and scope of the present invention.

What is claimed is:

1. A luer connector which comprises:
a main body portion;
a front luer portion;
an internally threaded locking ring that is axially slidable along the main body portion of the luer connector, the luer connector being adapted to couple to a mating luer device which has means for frictionally receiving the front luer portion and for threadedly receiving the internally threaded locking ring;
a collar carried by the luer connector between the main body portion and the front luer portion; and
a flexible member carried by the luer connector which flexible member flexes to a stressed position when the locking ring is in threaded engagement with the mating luer device, to provide some stress in the threaded engagement;
said flexible member being carried by the collar, to provide a resilient interrelationship between the collar and locking ring when the locking ring is in threaded engagement with the mating luer device;
said flexible member comprising a portion of the collar defined by a slot, which collar portion flexes to a stressed position by its engagement with an interior wall of the locking ring when the locking ring is in threaded engagement with the mating luer device.

2. A luer connector which comprises:
a main body portion;
a front luer portion;
an internally threaded locking ring that is axially slidable along the main body portion of the luer connector, the luer connector being adapted to couple to a mating luer device which has means for frictionally receiving the front luer portion and for threadedly receiving the internally threaded locking ring;
a collar carried by the luer connector between the main body portion and the front luer portion; and
a flexible member carried by the luer connector which flexible member flexes to a stressed position when the locking ring is in threaded engagement with the mating luer device, to provide some stress in the threaded engagement;
said flexible member being carried by the locking ring, to provide a resilient interrelationship between the collar and locking ring when the locking ring is in threaded engagement with the mating luer device;
said flexible member comprising an interior portion of the locking ring defined by a slot, which interior locking ring portion flexes to a stressed position by its engagement with the collar when the locking ring is in threaded engagement with the mating luer device.

3. A luer connector as described in claim 1, said collar defining an annular slot that is radially spaced from the center of the collar; said flexible member comprising an annular portion of the collar that is radially outward of the slot and is flexible when urged by an interior wall of the locking ring to tend to close the slot, thereby creating a spring that is hinged at the inside end of the slot.

4. A luer connector as described in claim 3, in which the annular portion of the collar carries a plurality of spaced protuberances for engagement with an interior wall of the locking ring.

5. A luer connector as described in claim 3, in which the annular slot has a radial width that is sufficient to prevent the slot from being closed when the interior wall of the locking ring engages the annular portion of the collar.

6. A luer connector as described in claim 4, in which the annular slot has a radial width that is sufficient to prevent the slot from being closed when the interior wall of the locking ring engages the spaced protuberances.

7. A luer connector as described in claim 1, in which the collar defines a slot which encircles the collar and opens upwardly to define an upstanding flexible member.

8. A luer connector as described in claim 7, in which the locking ring has an upper interior wall for surrounding the collar and a rear interior wall for engaging the upstanding flexible member.

9. A luer connector as described in claim 8, in which the rear interior wall carries a protuberance for engaging the upstanding flexible member.

10. A luer connector as described in claim 7, in which the slot has a width that is sufficient to prevent the slot from being closed when the rear interior wall of the locking ring engages the flexible member.

11. A luer connector as described in claim 2, in which the collar is stepped and the flexible member is adapted to engage one of the steps to flex and tend to close the slot.

12. A luer connector as described in claim 11, in which the slot has a width that is sufficient to prevent the slot from being closed when the flexible member is flexed by the engagement with the step.

13. A luer connector as described in claim 12, in which a stop member is carried by the interior portion of the locking ring for engagement with one of the steps to prevent excessive forward movement of the locking ring with respect to the collar.

14. In a luer connection system in which a male luer connector having a main body portion and a front luer portion is adapted for coupling to a mating female luer device and the male connector has a locking ring that is axially slidable along the main body portion and has interior threads which are adapted to threadedly engage the mating female luer device, the improvement comprising, in combination:

a collar carried by the male luer connector between the main body portion and the front luer portion; and a flexible member carried by one of the collar and locking ring to provide a resilient interrelationship between the collar and locking ring when the locking ring is in a threaded engagement with the mating female luer device, whereby the resilient interrelationship serves to provide some stress in the threaded engagement.

15. In a luer connection system as described in claim 14, said flexible member comprising a portion of the collar defined by a slot, which collar portion flexes to a stress position by its engagement with an interior wall of the locking ring when the locking ring is in threaded engagement with the mating luer device.

16. In a luer connection system as described in claim 15, said collar defining an annular slot that is radially spaced from the center of the collar; said flexible member comprising an annular portion of the collar that is radially outward of the slot and is flexible when urged by an interior wall of the locking ring to tend to close the slot, thereby creating a spring that is hinged at the inside end of the slot.

17. In a luer connection system as described in claim 15, said collar defining a slot which encircles the collar and opens upwardly to define an upstanding flexible member.

18. In a luer connection system as described in claim 17, said locking ring having an upper interior wall for surrounding the collar and a rear interior wall for engaging the upstanding flexible member.

19. In a luer connection system as described in claim 14, said locking ring carrying stop means for preventing excessive forward movement of the locking ring with respect to the collar; said collar being stepped and the flexible member being adapted to engage one of the steps to flex and tend to close the slot.

* * * * *

UNITED STATES PATENT AND TRADEMARK OFFICE
CERTIFICATE OF CORRECTION

PATENT NO. : 4,452,473
DATED : June 5, 1984
INVENTOR(S) : Ricky R. Ruschke

It is certified that error appears in the above-identified patent and that said Letters Patent are hereby corrected as shown below:

At column two, line four, delete "with" and substitute -- when -- therefor.

At column four, line five, delete the comma.

Signed and Sealed this

Second Day of October 1984

[SEAL]

Attest:

GERALD J. MOSSINGHOFF

Attesting Officer

Commissioner of Patents and Trademarks